United States Patent [19]
Zeppezauer et al.

[11] Patent Number: 5,780,432
[45] Date of Patent: Jul. 14, 1998

[54] THERAPEUTIC METHOD FOR TREATMENT OF CARCINOMA OR AUTOIMMUNE DISEASES

[75] Inventors: Michael Zeppezauer, Auf den Hutten, Germany; Reiner Class, Drexel Hill, Pa.

[73] Assignee: Allegheny University of the Health Sciences, Philadelphia, Pa.

[21] Appl. No.: 755,147

[22] Filed: Nov. 22, 1996

Related U.S. Application Data

[63] Continuation-in-part of Ser. No. 310,378, Sep. 22, 1994, Pat. No. 5,578,571, which is a continuation of Ser. No. 635,709, Dec. 28, 1990, abandoned.

[51] Int. Cl.⁶ .................. A61K 38/00; A61K 38/02; C07K 5/00; C07K 7/00
[52] U.S. Cl. .................. 514/12; 514/2; 530/324
[58] Field of Search ............. 514/2, 12; 530/324

[56] References Cited

U.S. PATENT DOCUMENTS

| | | | |
|---|---|---|---|
| 4,818,763 | 4/1989 | Rusch et al. | 514/2 |
| 4,902,505 | 2/1990 | Pardridge et al. | 424/85.7 |
| 5,578,571 | 11/1996 | Zeppezauer et al. | 514/12 |

*Primary Examiner*—Avis M. Davenport
*Attorney, Agent, or Firm*—Kanesaka & Takeuchi

[57] ABSTRACT

A therapeutic method for treatment of carcinoma or autoimmune diseases of a patient, which includes administering to said patient a biologically active composition which comprises a therapeutically acceptable carrier and, in a quantity having a therapeutic effect, two active substances comprising a pure cytostatic drug as the first active substance and a biologically active pure histone selected from the group consisting of H1, H2A, H2B, H2A:H2B, and H3 as the second active substance, providing a synergistic action of both of said active substances at a site of pathogenic process of said patient.

4 Claims, 21 Drawing Sheets

FIG. 16

TABLE 1

| CELL LINE | HISTONE (µg/ml) | CHEMOTHERAPEUTIC DRUG | LD50 DRUG ALONE (µg/ml) | LD50 WITH H1 (µg/ml) | REDUCTION IN DRUG CONCENTRATION (%) |
|---|---|---|---|---|---|
| DAUDI | 250 | BCNU | 6 | 0.3 | 95 |
| | | ADRIAMYCIN | 0.2 | 0.06 | 70 |
| | | BLEOMYCIN SULFATE | 8 | <0.004 | >99.9 |
| | | 5-FLUOROURACIL | 0.3 | <0.005 | >98.3 |
| | | CARBOPLATIN | 7 | 0.4 | 94.3 |
| | | METHOTREXATE | >2 | 2.3 | ud[1] |
| | | TAXOL | 0.02 | 0.002 | 90 |
| DAUDI | 150 | ETOPOSIDE | 5 | 0.52 | 89.6 |
| | | ADRIAMYCIN | 0.16 | 0.09 | 43.8 |
| | | CYTOSINE ARABINOFURANOSIDE | 0.2 | <0.2 | ud[2] |
| | | 5-FLUOROURACIL | 0.53 | 0.3 | 43.4 |
| | | METHOTREXATE | >20 | >20 | ud[3] |
| | | TAXOL | 0.033 | 0.013 | 60.6 |
| K562 | 250 | BCNU | >10 | <0.039 | ud[3] |
| | | ADRIAMYCIN | 2 | <0.015 | >99.3 |
| | | 5-FLUOROURACIL | >30 | <0.005 | ud[3] |
| | | CARBOPLATIN | >100 | <0.391 | ud[3] |
| | | METHOTREXATE | >20 | <0.078 | ud[3] |
| | | TAXOL | >10 | <0.002 | ud[3] |
| K562 | 150 | ETOPOSIDE | >200 | 30 | ud[1] |
| | | ADRIAMYCIN | 0.7 | <0.03 | >95.7 |
| | | CYTOSINE ARABINOFURANOSIDE | >50 | <0.2 | ud[3] |
| | | 5-FLUOROURACIL | >2 | <0.005 | ud[3] |
| | | METHOTREXATE | >20 | >20 | ud[3] |
| | | TAXOL | 1.05 | <0.002 | >99.8 |

THERAPEUTIC METHOD FOR TREATMENT OF CARCINOMA OR AUTOIMMUNE DISEASES

CROSS REFERENCE TO RELATED APPLICATIONS

This is a continuation-in-part application of Ser. No. 08/310,378 filed Sep. 22, 1994 now U.S. Pat. No. 5,578,571, which is a continuation of Ser. No. 07/635,709 filed Dec. 28, 1990, now abandoned.

BACKGROUND OF THE INVENTION

Cytostatic drugs have been used for the therapy of malignant diseases. The successful therapy of neoplastic diseases depends on early diagnosis and removal of tumors. Radiation therapy is applied for locally restricted tumors and is also combined with surgical therapy. In the case of disseminating tumors and metastases, treatment is restricted to chemotherapy and immunotherapy. Chemotherapeutic treatments are usually accompanied by severe side effects such as damage of the kidneys and liver, disturbances of the hematopoietic system and other kinds of damage impairing the patient's general well-being and resistance. In addition, most cytostatic agents act as strong immunosuppressive agents. These side effects often necessitate a dosage of cytostatic which is not sufficiently high for the therapeutic purpose, or they demand an interruption of the treatment.

The prolonged use of cytostatic drugs often leads to the selection of resistant cancer cells which ultimately cause the death of the patient. Finally, these are cancer cells which are totally insensitive against the known cytostatic agents.

Immunotherapy based on interferons and interleukins is applied mainly in order to stimulate the cellular resistance. In general immunotherapy consists of supportive, additive measures without independent therapeutic potential in the malignant process. The immunosuppressive effect of cytostatic substances has rendered them useful in the therapy of autoimmune diseases such as multiple sclerosis, psoriasis and certain rheumatic diseases. Even here their beneficial effect has to be weighed against the serious side effects which necessitate too low dosages and/or interruption of the treatment.

SUMMARY OF THE INVENTION

Accordingly, it is an object of the present invention to provide a combination of active substances which produces a significantly improved cytostatic or cytotoxic effect as compared to conventional cytostatic, such as vincristine, methotrexate, cisplatin, given alone. Thereby, chemotherapies may be offered which combine increasing efficiency with a large reduction of side effects and therapeutic doses. Thus, the therapeutic efficiency of known cytostatic drugs is increased. Also, certain cell lines which are insensitive to chemotherapeutic treatment may become susceptible to chemotherapy by applying the combination of active substances.

The European patent application 85100179.2 discloses that at least one histone and/or one histone fragment may show hormonal effect which may be used favorably in the treatment of cancer. This applies in particular to the histones H1, H2A and/or H2B and H3.

In the German patent application publication 3737274, the direct cytotoxic action on certain cancer cell lines of the mixture of histones H2A/H2B has been demonstrated. The cytotoxic action on certain malignant cell lines of histone H1 has been demonstrated in the U.S. Pat. application Ser. No. 07/332,658 filed Apr. 3, 1989. The application is a CIP application of the U.S. Pat. application Ser. No. 777,783 filed Jan. 10, 1985, issued as U.S. Pat. No. 4,818,763.

The object is achieved by the invention as defined in the claims given at the end of the specification.

BRIEF DESCRIPTION OF THE DRAWINGS

The efficiency of a combination of active substances according to the invention is demonstrated by the results of the following experiments visualized by the accompanying drawings, wherein

FIG. 16 is a table showing summary of the cytotoxicity experiments.

DESCRIPTION OF THE PREFERRED EMBODIMENT

Figure 1:
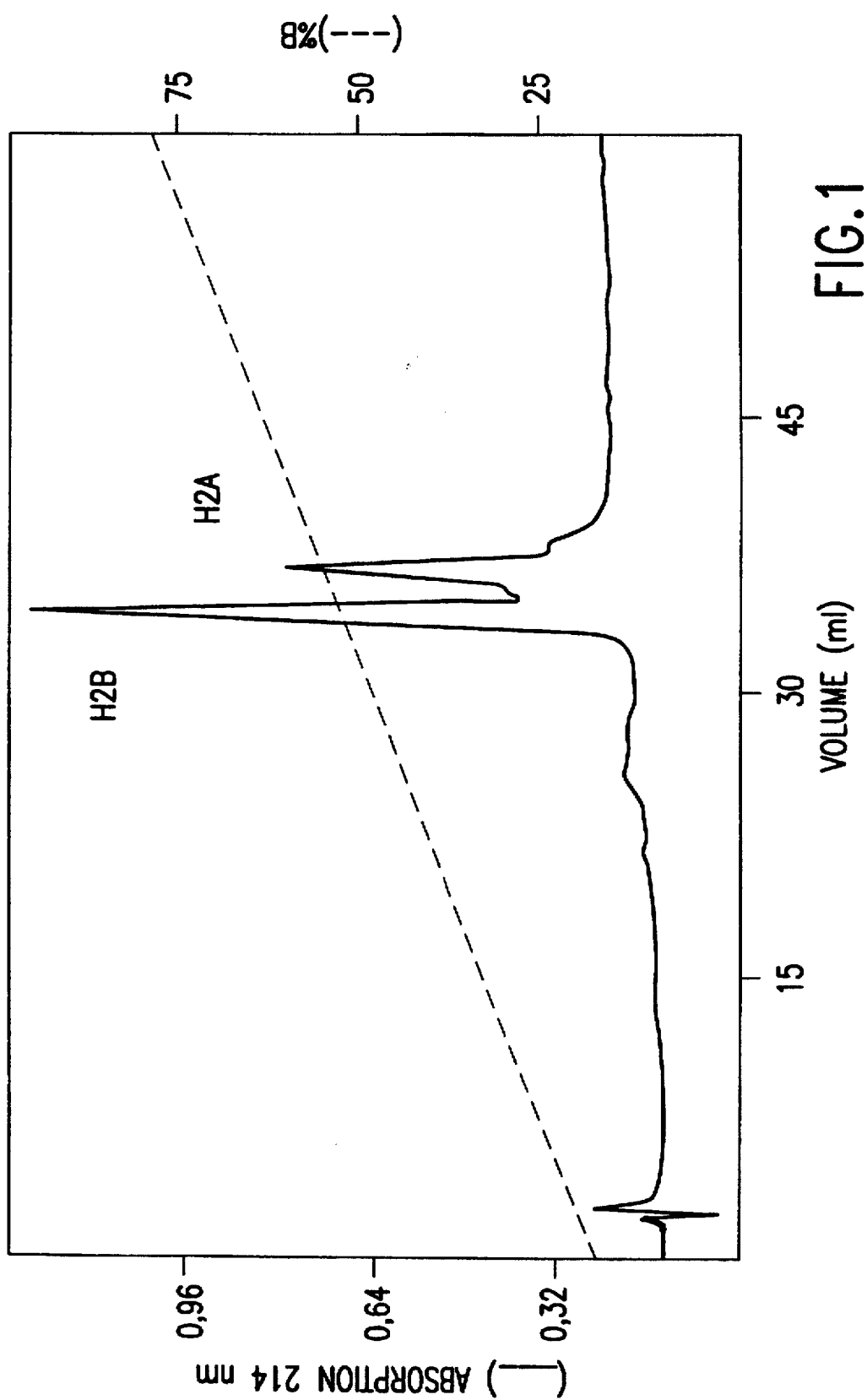
FIG. 1 is a graph showing the absorption by histones H2A and H2B.

In FIG. 1, a mixture or complex of histones H2A and H2B was used. It had been obtained by High Performance Lignid Chromatography (HPLC) from a preparation of the Homeostatic Thymus Hormone from calf thymus (Bernardi G. & Comsa J., Purification chromatographigne d'une preparation de thymus donee d'activite hormonale, Experienta 21, 416–417, 1965).

Elution was performed from a uBondapak C18 column using a linear gradient (%B) from 20 to 80% acetonitrile in 0.1% trifluoro acetic acid. The flow rate was 1 ml/min. The eluate was monitored by measuring the optical absorption at 214 nm. In FIG. 1, on the abscissa, the effluent volume is depicted on the left ordinate, the absorption at 214 nm, and on the right ordinate, the linear gradient (%B).

Accordingly, the pure histones H2A and H2B can be prepared. It remains to be shown whether H2A:H2B (FIG.

1) is a mixture of H2A and H2B or a chemical complex of both molecules. It is obvious that other known procedures for the preparation of pure histones may be used. Thus the invention is not restricted to the utilization of H2A:H2B; rather, it includes their active parts or fragments with cytostatic and cytotoxic effect. Although the mechanism of the cytotoxic or cytostatic action of histones or of their active parts or fragments is not yet understood the inventors have reasons to believe that the repetitive amino acid sequences KRAA and KRVA and their environments play an active part in the biological action of said molecules. The sequence KRAA is found in the C-terminal part of histone H1 and the sequence KRVA is found in the N-terminal part of histone H2B.

The malignant cells were grown in culture medium completed with fetal calf serum (FCS). The culture medium RPMI 1640 with 10% FCS was renewed daily. When the bottom of the culture flask was covered completely with cells, these were scratched off gently and partly transferred to another flask in order to obtain cells under optimal growth conditions. Incubation was performed at 36.50° C. and 5.5% carbon dioxide in a controlled incubator.

The concentration of living cells was determined using the dye Nigrosin (0.2% in phosphate-buffered saline; i.e., PBS) in the Neubauer chamber.

The components of the combined chemotherapeutic agent according to this invention (e.g., H2A:H2B and a known cytostatic agent) were added to the culture medium either alone or combined according to the invention and the solutions were subjected to sterile filtration.

For the purpose of the experiments the malignant cells were scratched off the bottom of those culture flasks which were not covered too tightly by cells. The number of living cells was determined and adjusted to $3.5 \times 10^5$ cells/ml. Part of this cell suspension was mixed with the combined chemotherapeutic agent or its single components and placed in the incubator. The final concentration of malignant cells was $1.75 \times 10^5$ cells/ml in each well.

Experiment 1

Figure 2:
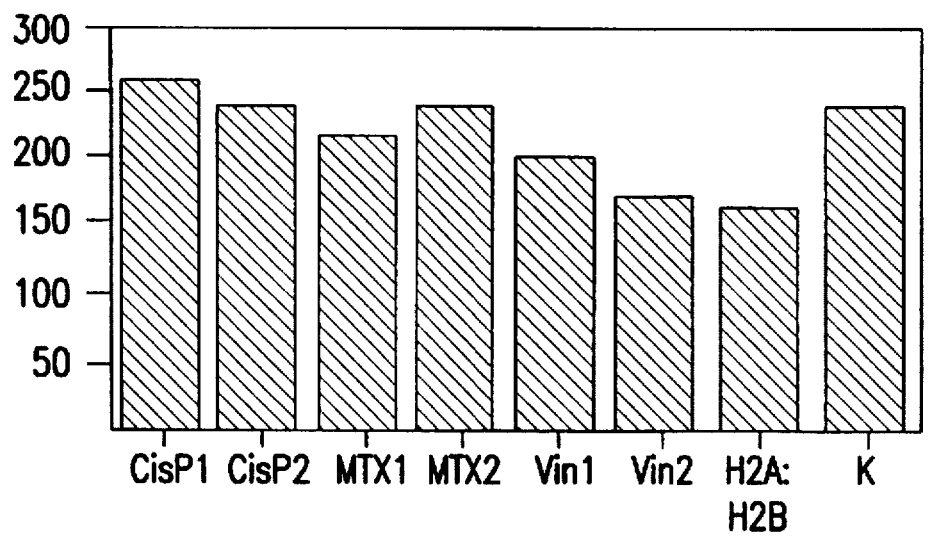
FIG. 2 is a graph showing the growth of lymphoma cell line with respect to various agents.

The lymphoma cell line OH77 was used to test the efficiency of the combination of H2A:H2B with either cisplatin or methotrexate, or vincristine. FIG. 2 shows the results of this cytotoxicity test with the cytostatic agents and H2B:H2A alone. Cells of the cell line OH77 were incubated for 48 hours with 1 µg/ml cisplatin (CisPl), or 2 µg/ml methotrexate (MTX2), or 5 µg/ml vincristine (Vinl), or 10 µg/ml vincristine (Vin2) or 250 µg/ml H2A:H2B, and the growth rate was determined in percent. K indicates the control experiment where the growth rate was determined without addition of a cytostatic agent or H2A:H2B for 48 hours. The cytostatic agents alone or H2A:H2B alone showed small or no cytostatic effects at all.

Figure 3:
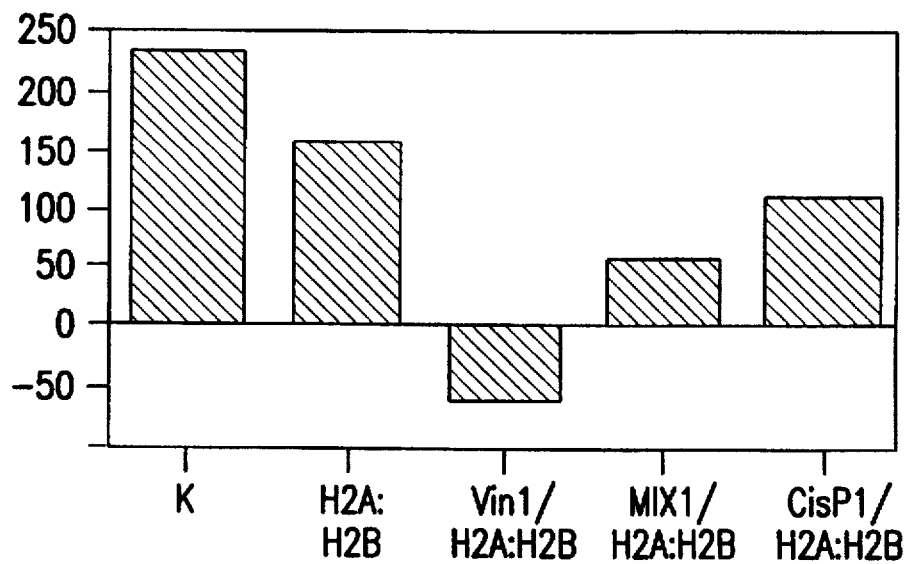
FIG. 3 is a graph showing the growth of lymphoma with respect to various agents.

FIG. 3 shows another cytotoxicity test in which each of the above-mentioned cytostatic was used in combination with H2A:H2B. Cells of the OH77 cell line were incubated for 48 hours with 100 µg/ml H2A:H2B and 5 µg/ml vincristine (Vin1/H2A:H2B), or 5 µg/ml methotrexate (MTX1/H2A:H2B), or 1 µg/ml cisplatin (CisPl/H2A:H2B) and the growth rate was determined. K depicts again the growth rate for 48 hours in the absence of any agent. For better comparison the cytostatic effect of 100 µg/ml H2A:H2B alone is also shown.

A clear synergistic action resulting in a cytotoxic effect is demonstrated by combining vincristine and H2A:H2B in concentrations each of which alone shows only a slight cytostatic effect (FIG. 2).

An improvement of the cytostatic action by the combination of H2A:H2B with methotrexate or with cisplatin is seen compared to the action of the components alone. This is particularly clear in the case of methotrexate.

Experiment 2

Figure 4:
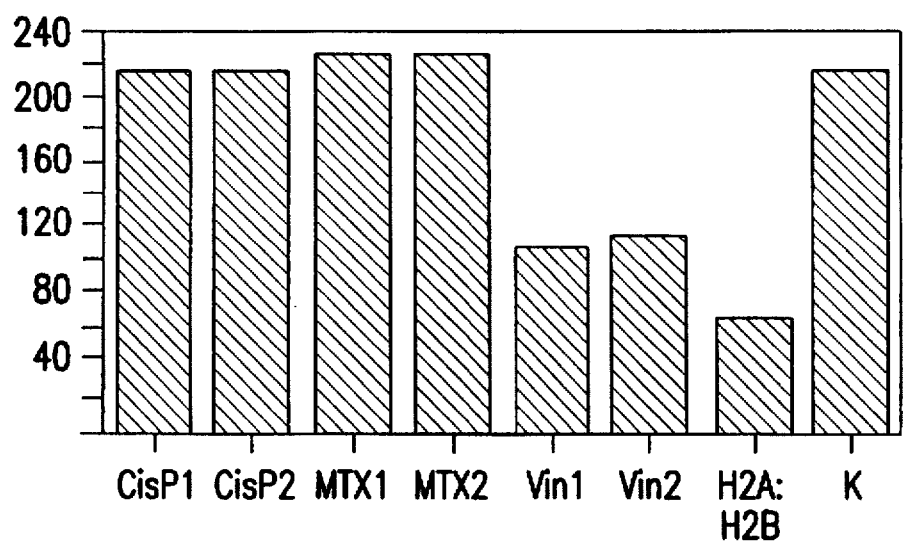
FIG. 4 is a graph showing the growth of melanoma cell line with respect to various agents.

The efficiency of H2A:H2B combined with the above-mentioned cytostatic drugs was also tested in vitro with the melanoma cell line EG 463. FIG. 4 shows the results of a cytotoxicity test with said cytostatic and H2A:H2B alone. Cells of the melanoma cell line EG 463 were incubated for 48 hours with the following substances alone and the growth rate was noted in %.

CisPl=1 µg/ml cisplatin,

CisP2=2 µg/ml cisplatin,

MTX1=5 µg/ml methotrexate,

MTX2=10 µg/ml methotrexate,

Vin1=5 µg/ml vincristine,

Vin2=10 µg/ml vincristine, and

H2A:H2B=250 µg/ml H2A:H2B.

K depicts again the control experiment devoid of any agent.

Figure 5:
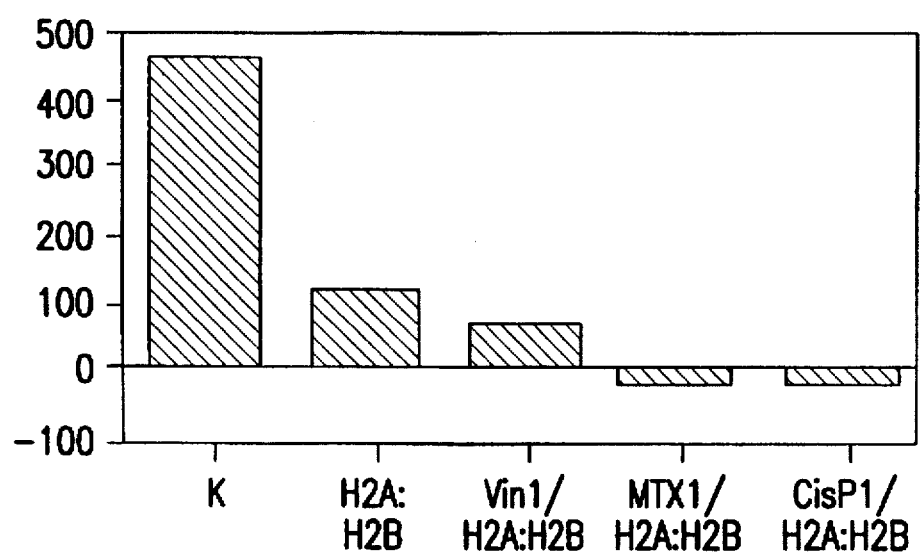
FIG. 5 is a graph showing the growth of melanoma with respect to various agents.

In FIG. 5, the cells of the melanoma cell line EG 463 were incubated for 48 hours with the above-mentioned cytostatic agents in combination with H2A:H2B and the growth rate was determined:

Vin1/H2A:H2B=5 µg/ml vincristine+100 µg/ml H2A:H2B

MTX1/H2A:H2B=5 µg/ml methotrexate+100 µg/ml H2A:H2B

CisP1/H2A:H2B=1 µg/ml cisplatin+100 µg/ml H2A:H2B

K depicts again the control experiment devoid of any addition and H2A:H2B shows the cytostatic action of 100 µg/ml H2A:H2B alone. It is evident from FIG. 5 that the combination of H2A:H2B and vincristine which each exert a slightly cytostatic action (FIG. 4) is characterized not by a synergistic effect but rather a mere additive one.

In contrast, methotrexate and cisplatin, when given alone, are inefficient (FIG. 4) show a cytotoxic effect when each of them is administrated in combination with H2A:H2B. This again demonstrates the synergism resulting from the combination of H2A:H2B with methotrexate and cisplatin, respectively.

Experiment 3

Figure 6:
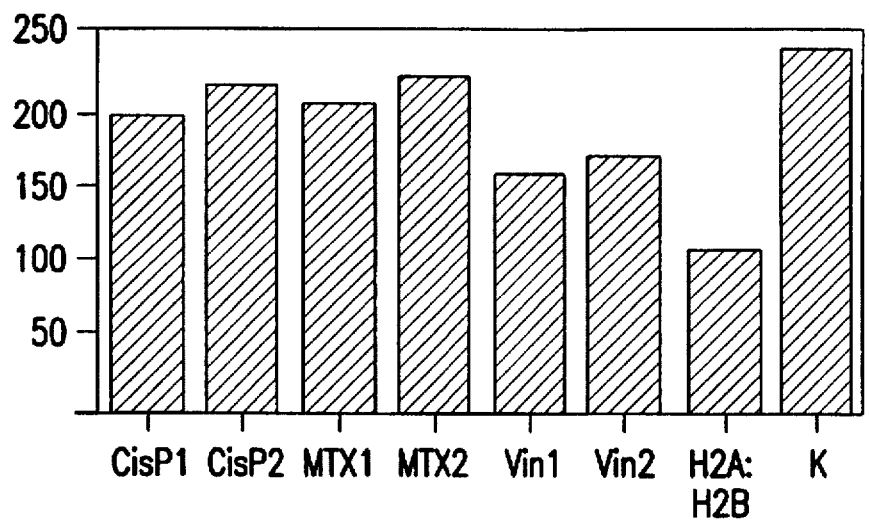
FIG. 6 is a graph showing the growth of Hufibl fibroblort cell with respect to various agents.

The efficiency against nontransformed human fibroblasts was tested in vitro using the combination of H2A:H2B with the above-mentioned cytostatic drugs. FIG. 6 shows the data obtained with either the cytostatic agents or the H2A:H2B alone which were tested against the Hufibl fibroblast cell line. Cells of this cell line were incubated for 48 hours with one of the following substances and the growth rate was monitored and expressed in %.

Cispl=1 µg/ml cisplatin,

CisP2=2 µg/ml cisplatin,

MTX1=5 µg/ml methotrexate,

MTX2=10 µg/ml methotrexate,

Vinl=5 µg/ml vincristine,

Vin2=10 µg/ml vincristine, and

H2A:H2B=250 µg/ml H2A:H2B.

K depicts again the control experiment without any additive for 48 hours.

Figure 7:
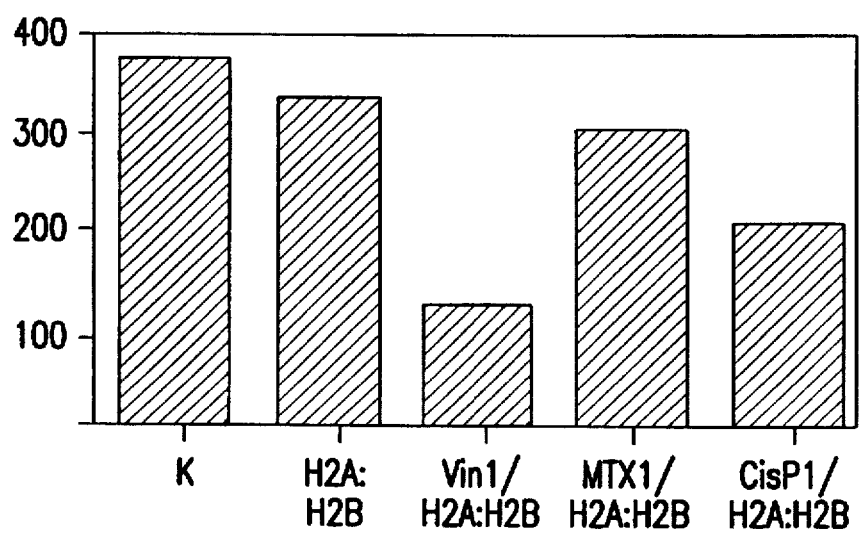
FIG. 7 is a graph showing the growth of Hufibl fibroblort with respect to various agents.
Figure 8A:
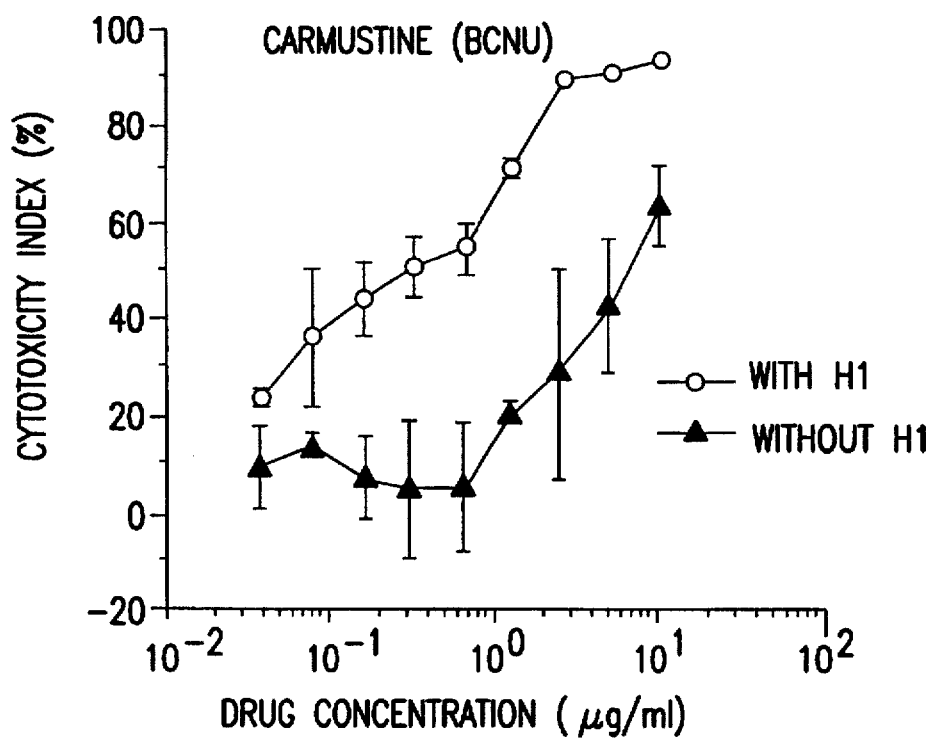
FIGS. 8A, 8B, 8C and 8D are graphs showing cytotoxicity indexes with respect to various drugs.
Figure 8B:
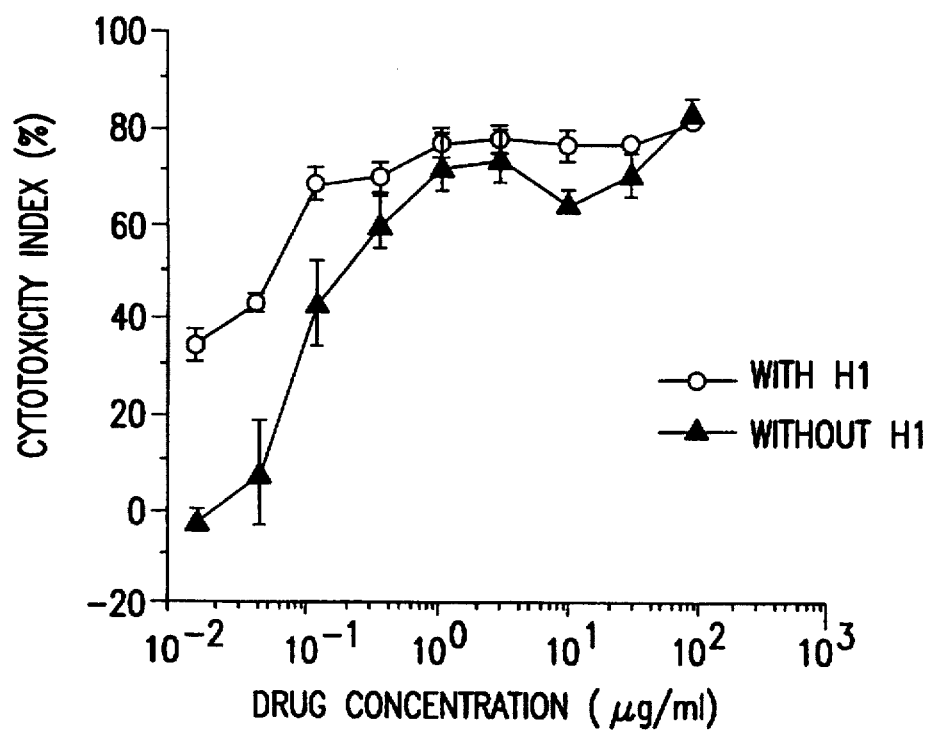
Figure 8C:
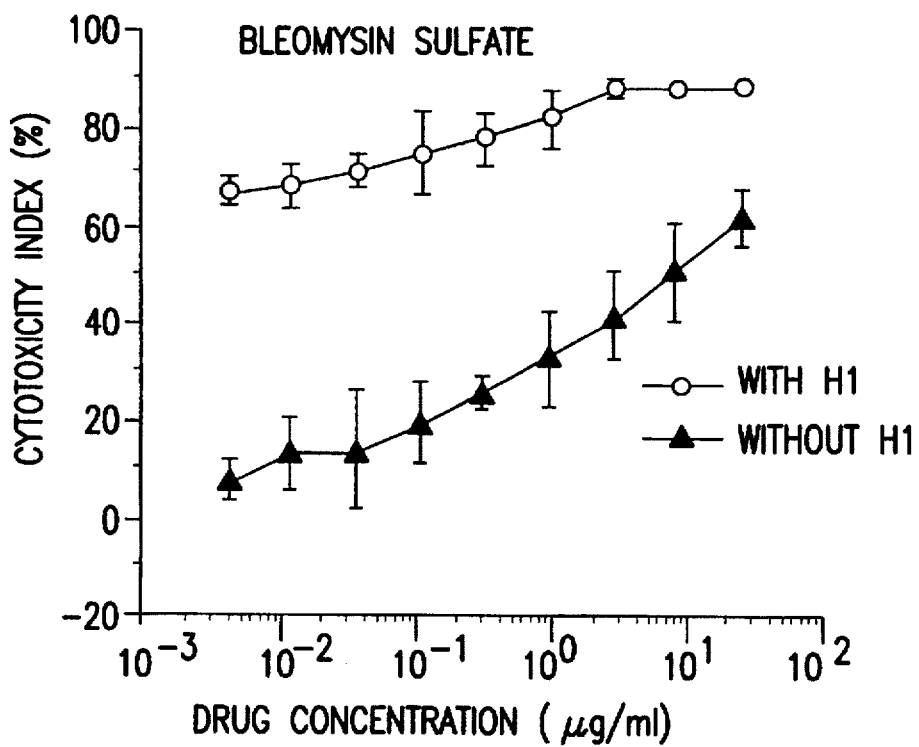
Figure 8D:
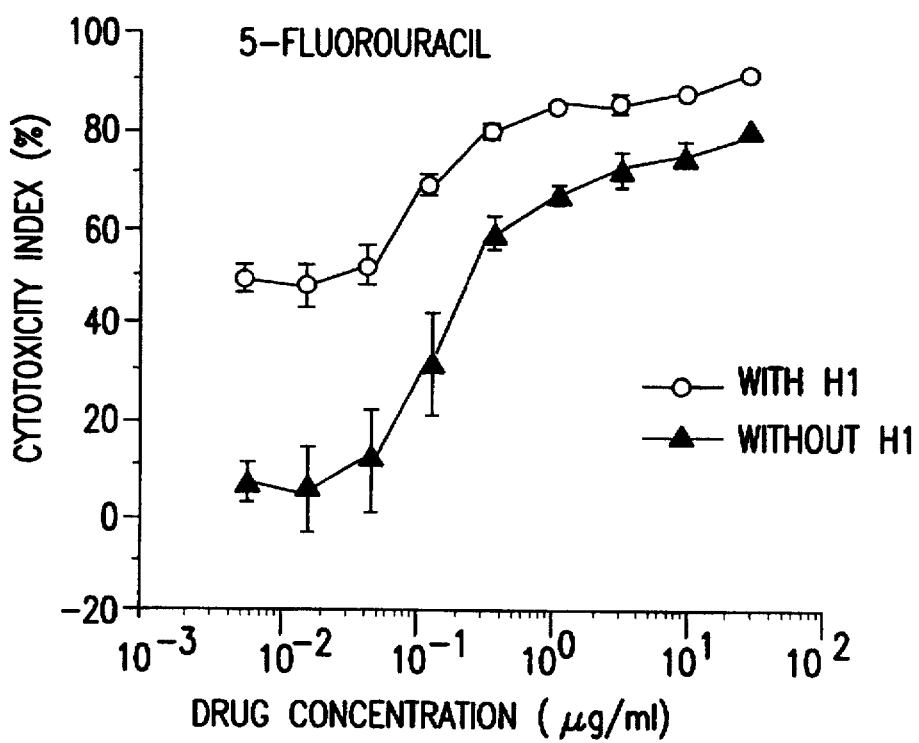

In FIG. 7, the data are obtained by incubating for 48 hours cells of the human fibroblast line Hufibl with one of the above-mentioned cytostatic agents combined with H2A:H2B and monitoring the growth rate as follows:

Vin1/H2A:H2B=5 µg/ml vincristine+100 µg/ml H2A:H2B,

MTX1/H2A:H2B=5 µg/ml methotrexate+100 µg/ml H2A:H2B, and

CisP1/H2A:H2B=1 µg/ml cisplatin+100 µg/ml H2A:H2B

In addition the above-mentioned cell line was incubated solely with 100 µg/ml H2A:H2B for comparison. K depicts again the control experiment devoid of any addition.

The data show that no synergistic effect is observed upon the combined action of H2A:H2B and cytostatic agents against non-transformed human fibroblasts. The measurable cytostatic action of the cytostatic compounds is enhanced by H2A:H2B (FIG. 7) but it is not changed into a cytotoxic one.

Additional Experiments

Cells from established cell lines of different hemopoietic lineage derived from a leukemia patient with Burkitt's lymphoma (DAUDI) or erythroleukemia (K562) were tested in a survival assay in the presence of the following clinically used chemotherapeutic drugs:

Carmustine (BCNU), Adriamycin, Bleomycin Sulfate, 5-Fluorouracil, Paraplatin (Carboplatin), Methotrexate, Taxol (Paclitaxel), Etoposide, Cytosine Arabinofuraoside (Are-C).

Cells were seeded in a 96-well flat bottom microtiter plate at 100 µl/well and $2 \times 10^5$/ml in RPMI 1640 containing 10% (v/v) heat inactivated fetal calf serum, 2 mM L-Glutamine, 0.2% (w/v) $NaHCO_3$, 20.000 IU streptomycin sulfate/L, and 20.000 IU penicillin G/L. Chemotherapeutic drugs were added at 50 µl/well to give a final concentration as indicated in table 1 in FIG. 16. Histone H1 was added at 50 µl H1/well to give a final concentration of 150 or 250 µg/ml final. Media alone was used instead of histone H1 as control. The plates were incubated for 48 hours at 37° C. and 5% $CO_2$. The viability of the cells was determined using the Alamar Blue assay (reduction related to cell growth causes the alamar blue indicator to change from the oxidized (non-fluorescent, blue) to the reduced (fluorescent, red) form) by adding 10% (v/v) Alamar Blue/well for 4 hours at 37° C. and 5% $CO_2$. The plates were assayed in a fluorimeter at 560 nm excitation and 570 nm emission. The viability was expressed as cytotoxicity index (CI) and was determined according to the following formula:

$$CI = (1 - EM_{570} \text{ with H1})/(EM_{570} \text{ without H1})) * 100$$

The dose of the chemotherapeutic drug+histone H1 needed to result in a 50% cell killing (CI=50) is called the LD50. The dose of the chemotherapeutic drug to reach 50% cell killing (=LD50) was determined graphically and compared to the LD50-dose of chemotherapeutic drug in combination with histone H1 (at 150 or 250 µg/ml, respectively) and expressed in table 1 as percentage reduction in drug concentration. The results are shown in the following graphs.

FIGS. 8A, 8B, 8C, and 8D show cytotoxicity indexes of different concentrations of BCNU (A), Adriamycin (B), Bleomycin Sulfate (C), and 5-Fluorouracil (D) with and without histone H1 250 µg/ml used in co-culture with cells of the Burkitt's lymphoma cell line DAUDI.

Figure 9A:
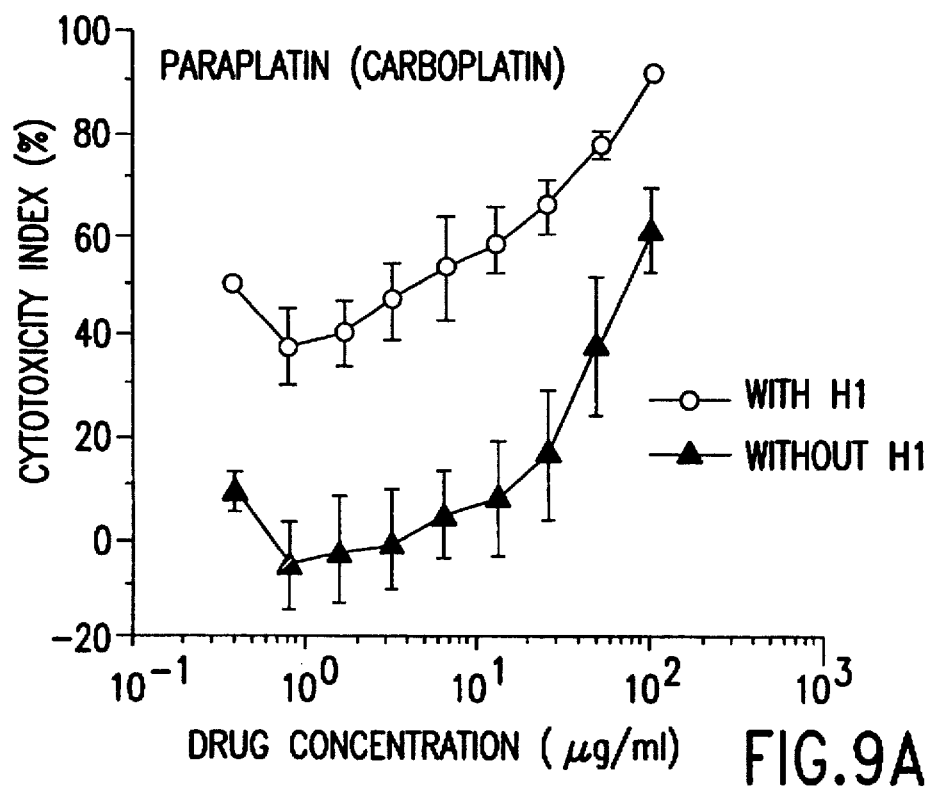
FIGS. 9A, 9B, and 9C are graphs showing cytotoxicity indexes with respect to various drugs.
Figure 9B:
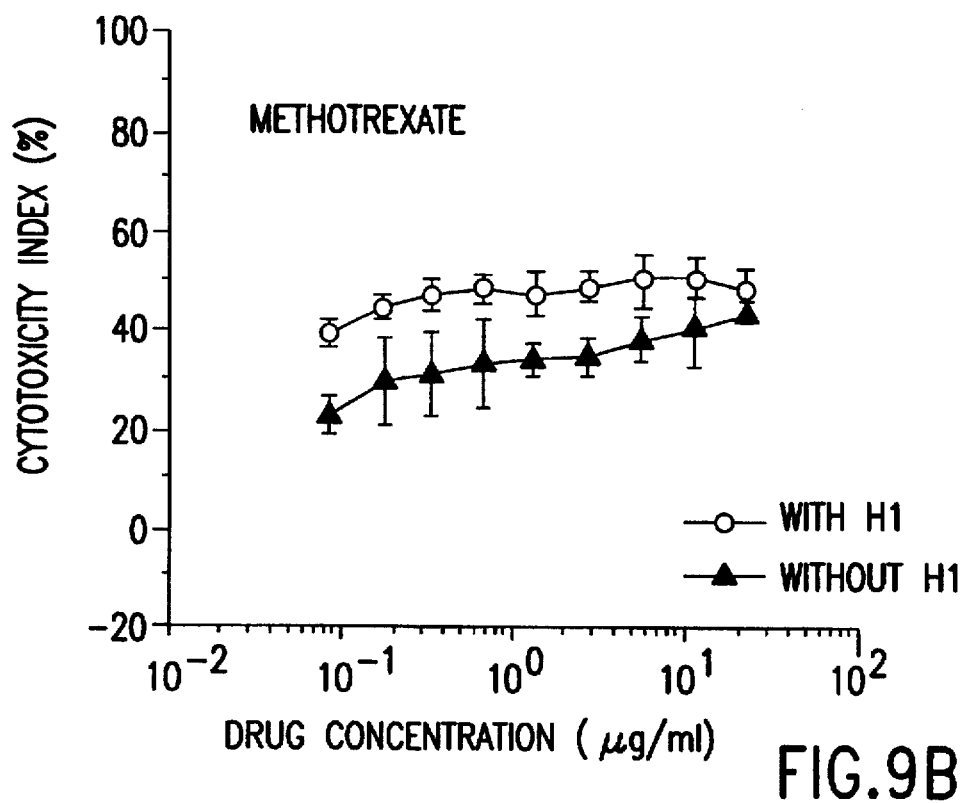
Figure 9C:
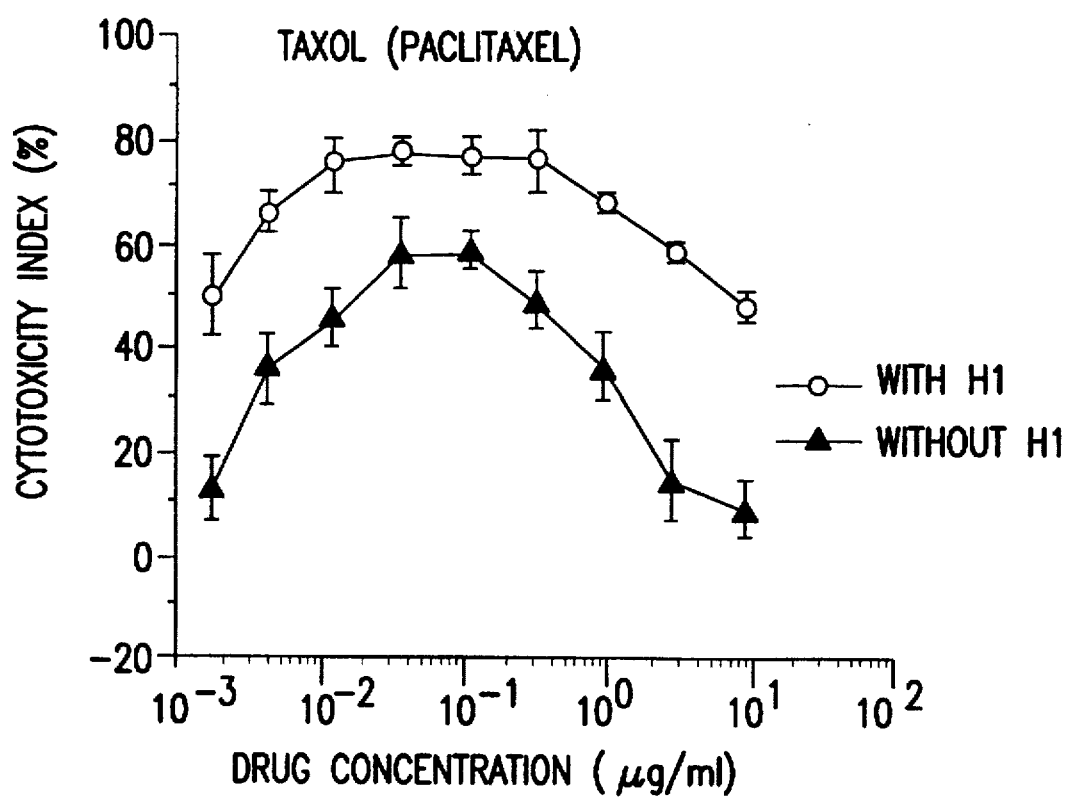

FIGS. 9A, 9B, and 9C shows cytotoxicity indexes of different concentrations of Paraplatin (A), Methotrexate (B), and Taxol (C) with and without histone H1 250 µg/ml used in co-culture with cells of the Burkitt's lymphoma cell line DAUDI.

Figure 10A:
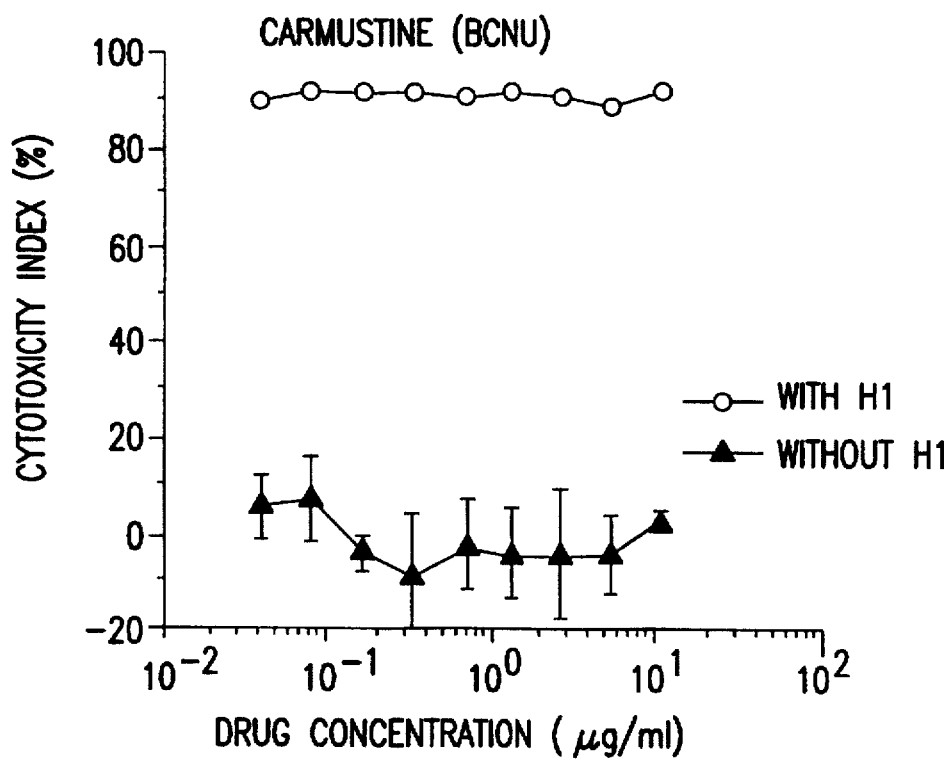
FIGS. 10A, 10B, and 10C are graphs showing cytotoxicity indexes with respect to various drugs
Figure 10B:
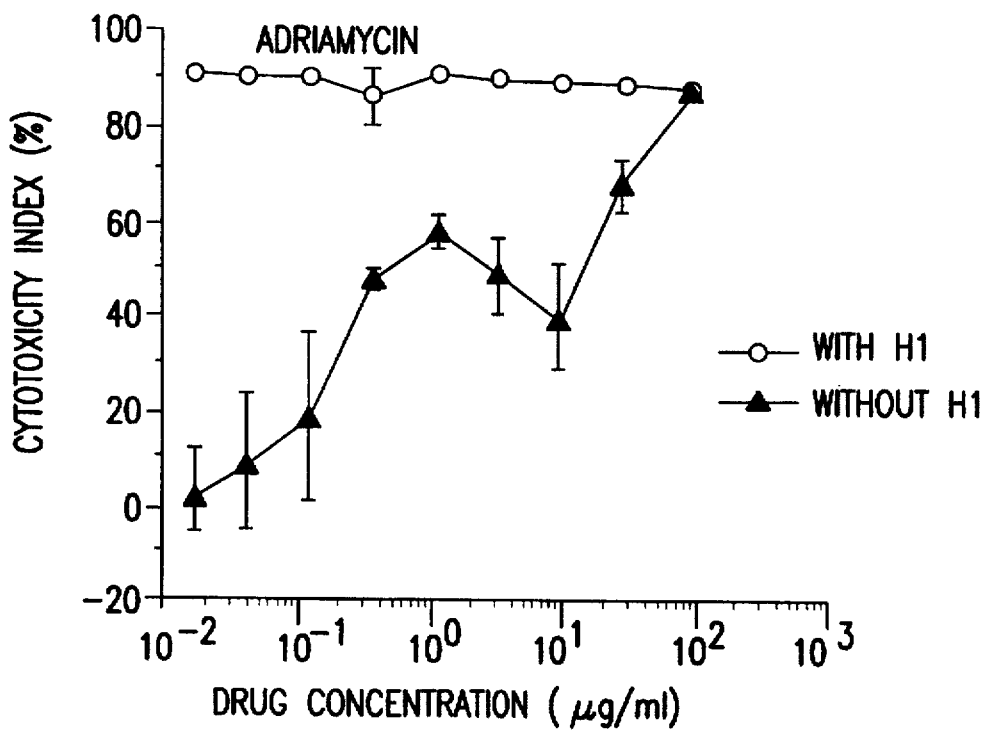
Figure 10C:
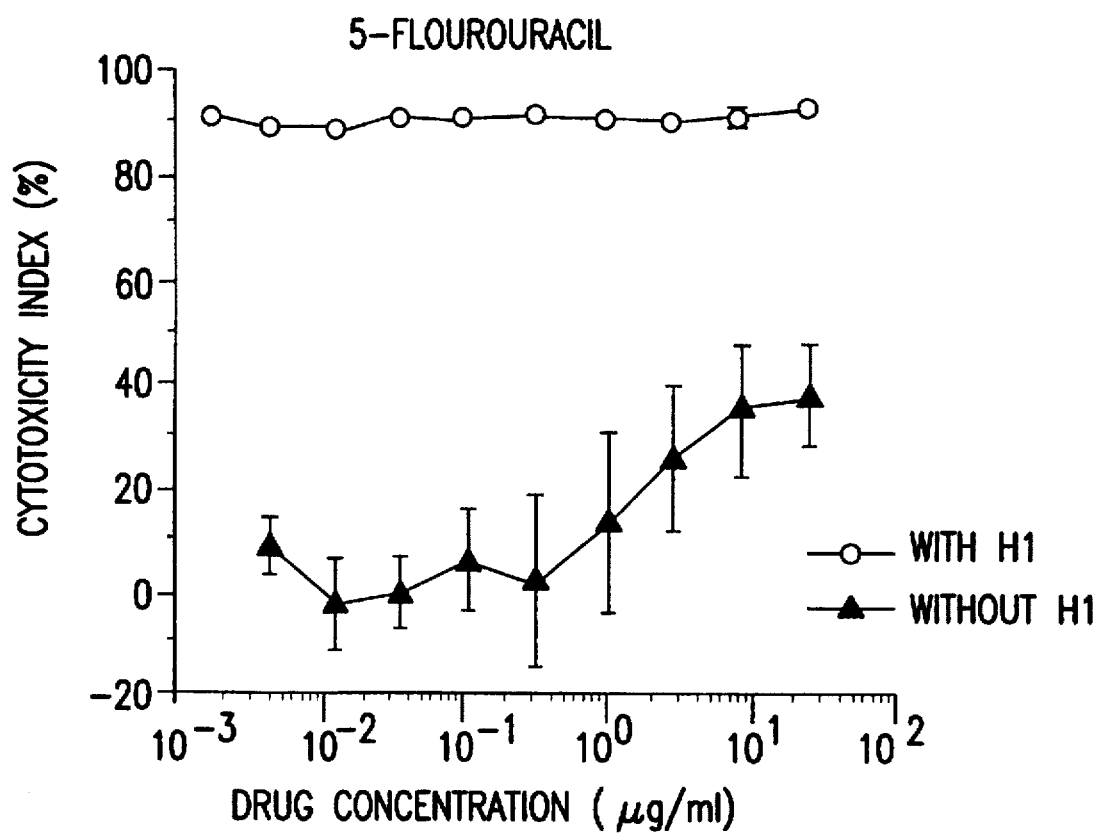

FIGS. 10A, 10B, and 10C show cytotoxicity indexes of different concentrations of BCNU (A), Adriamycin (B), and 5-Fluorouracil (C) with and without histone H1 250 µg/ml used in co-culture with cells of the erythroleukemia cell line K562.

Figure 11A:
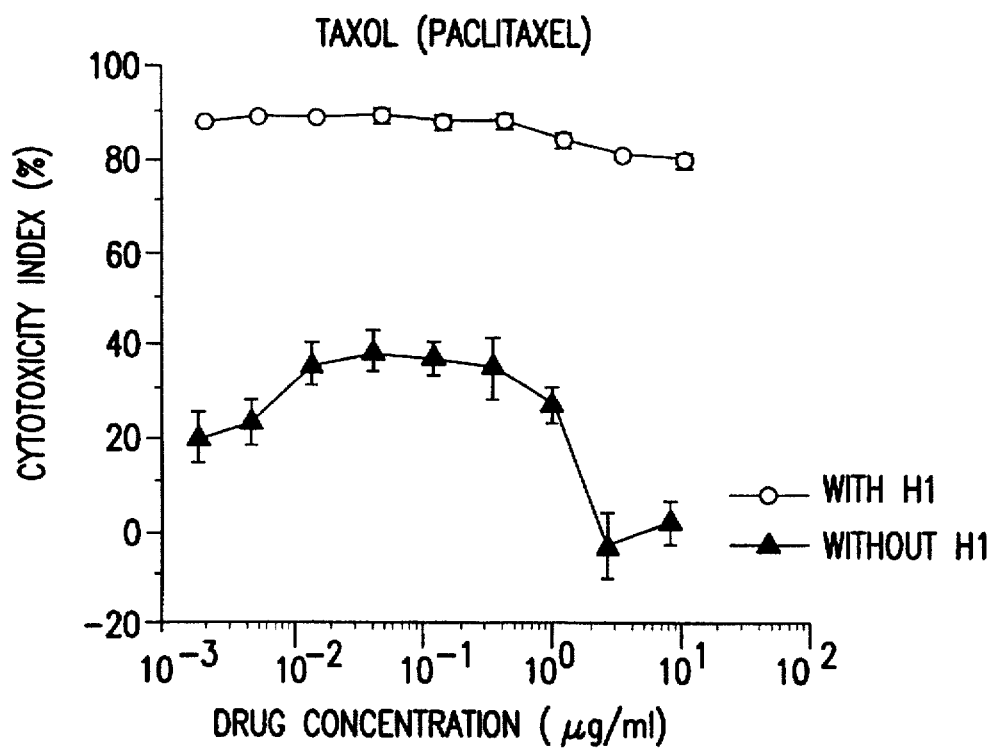
FIGS. 11A, 11B, and 11C are graphs showing cytotoxicity indexes with respect to various drugs.
Figure 11B:
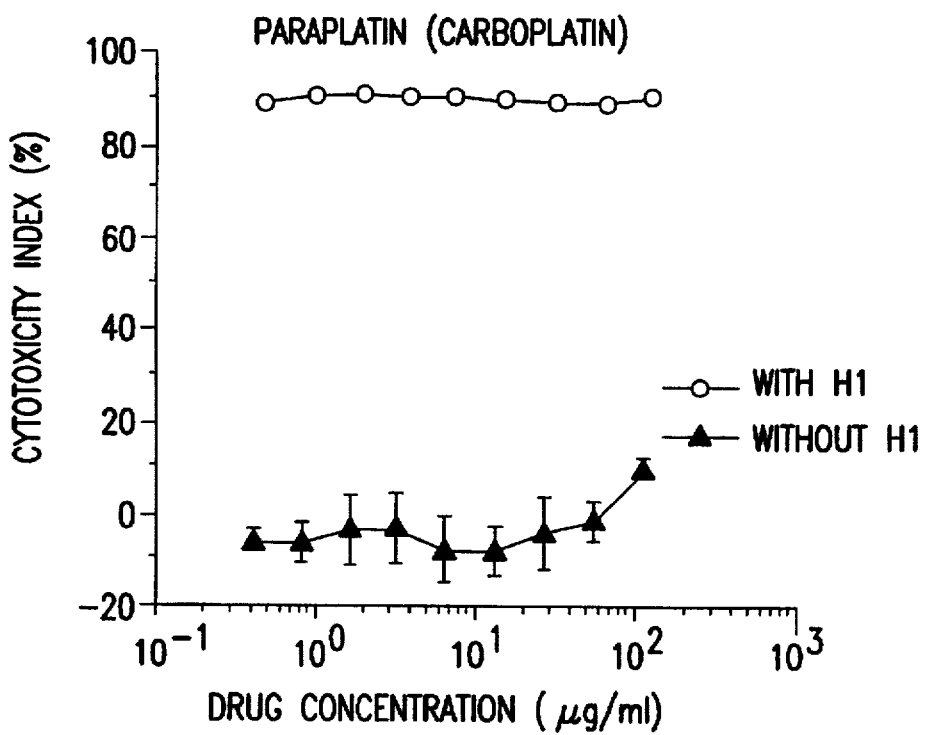
Figure 11C:
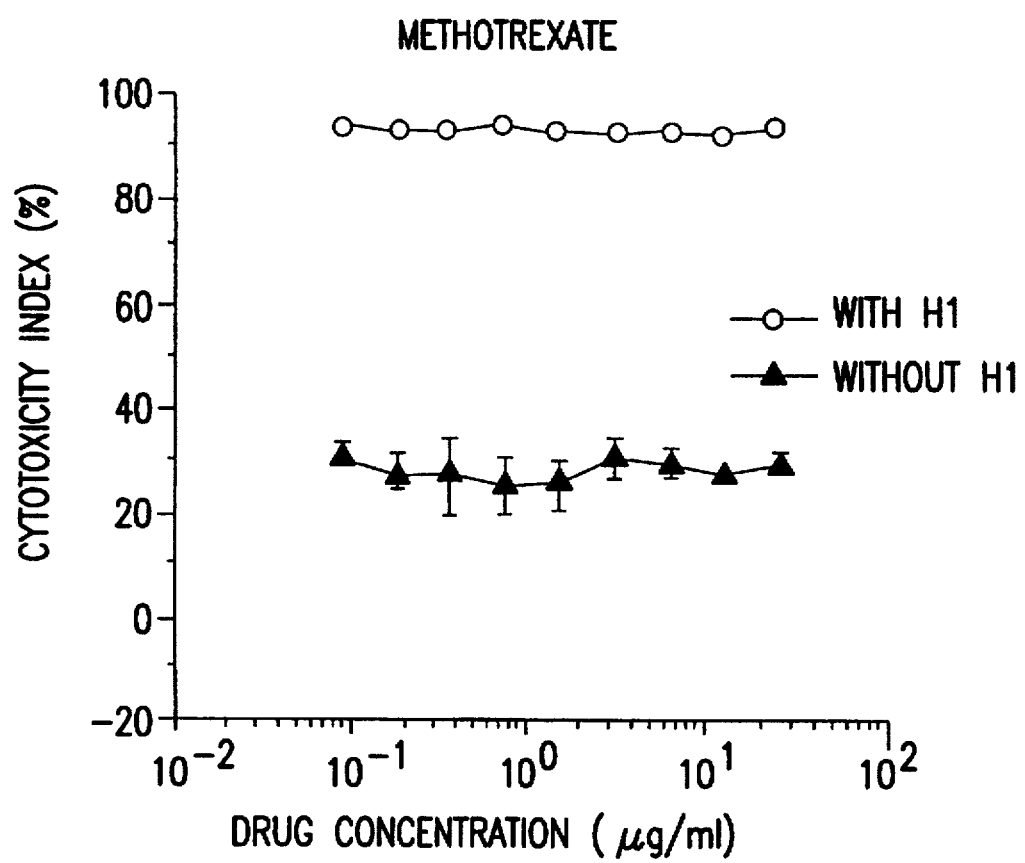

FIGS. 11A, 11B, and 11C shows cytotoxicity indexes of different concentrations of Taxol (A), Paraplatin (B), and Methotrexate (C) with and without histone H1 250 µg/ml used in co-culture with cells of the erythroleukemia cell line K562.

Figure 12A:
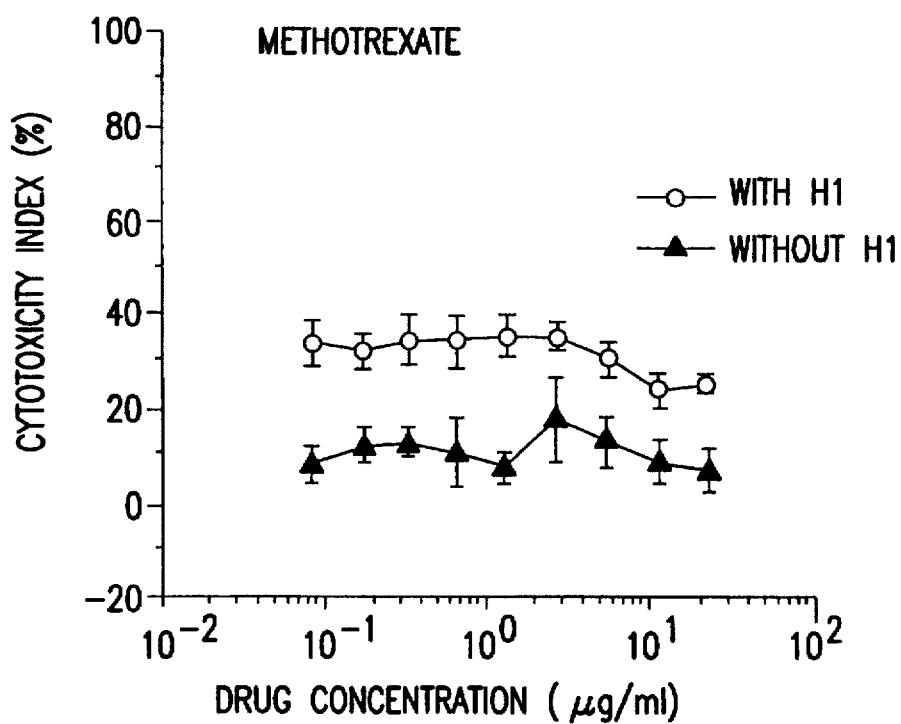
FIGS. 12A, 12B, and 12C are graphs showing cytotoxicity indexes with respect to various drugs.
Figure 12B:
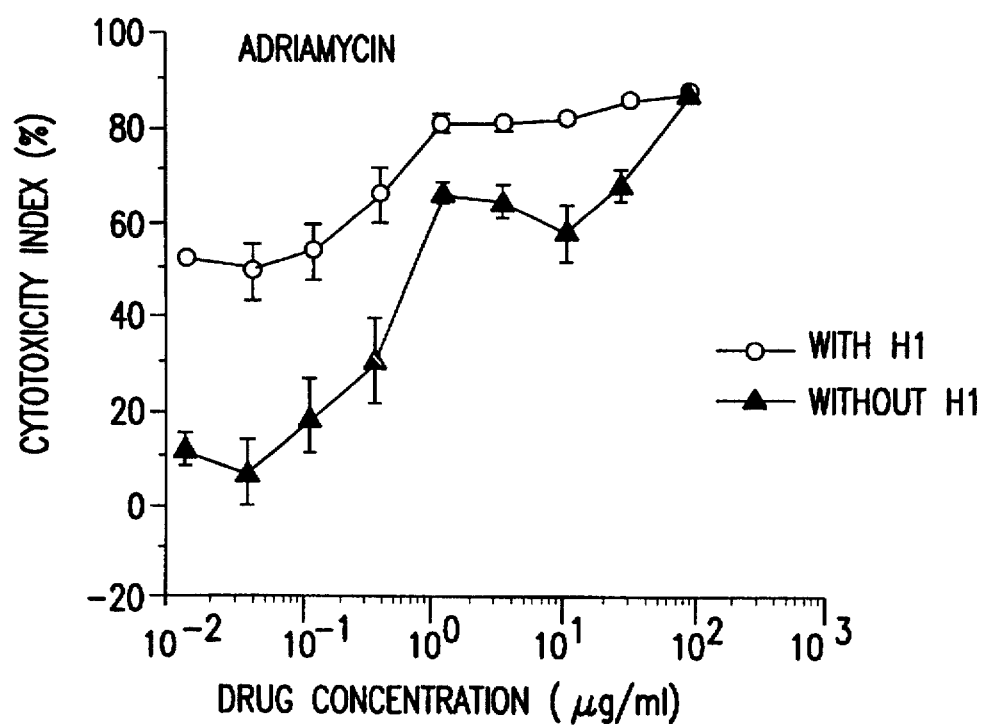
Figure 12C:
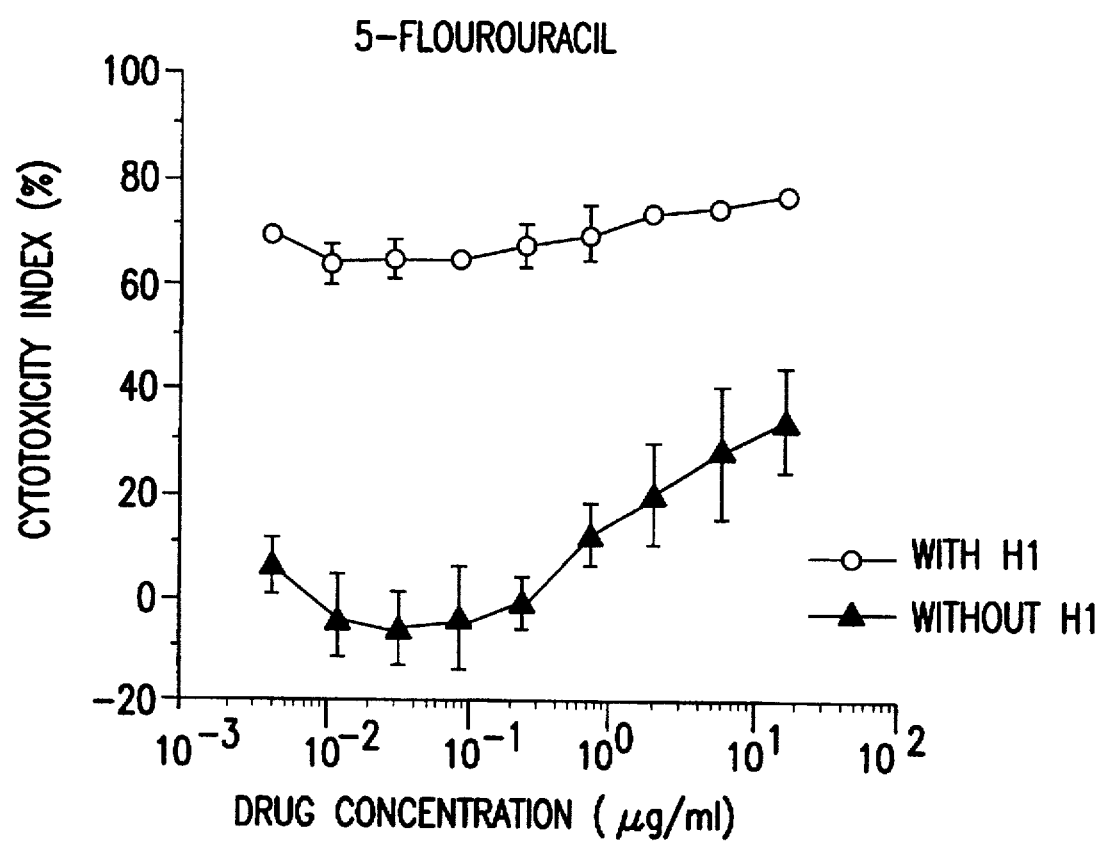

FIGS. 12A, 12B, and 12C show cytotoxicity indexes of different concentrations of Methotrexate (A), Adriamycin (B), and 5-Fluorouracil (C) with and without histone H1 150 µg/ml used in co-culture with cells of the Burkitt's lymphoma cell line DAUDI.

Figure 13A:
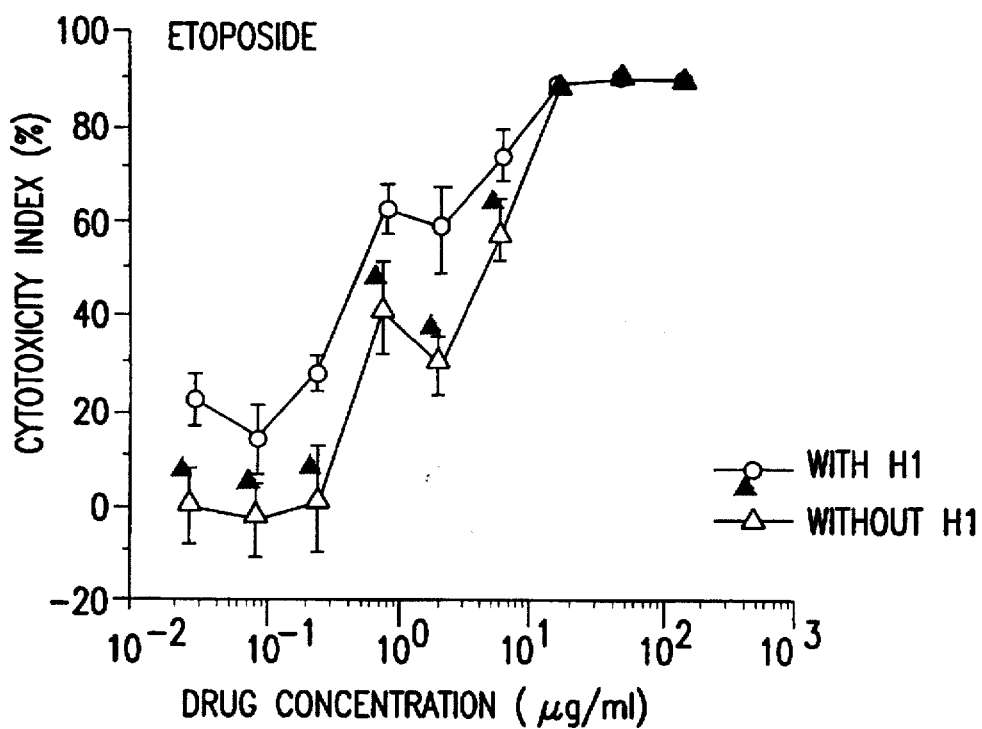
FIGS. 13A, 13B, and 13C are graphs showing cytotoxicity indexes with respect to various drugs.
Figure 13B:
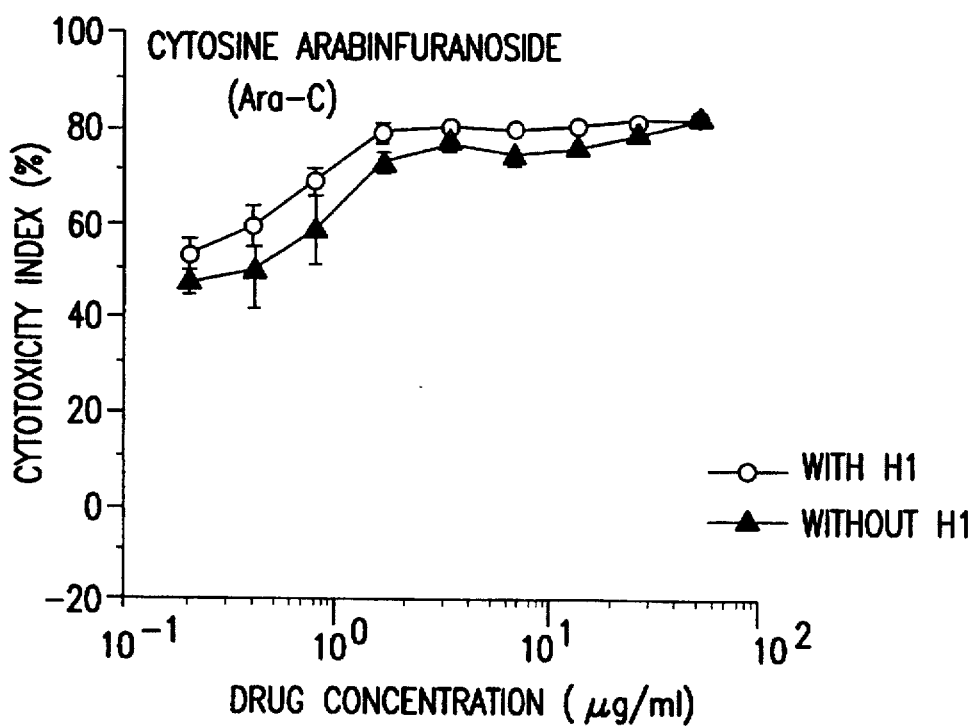
Figure 13C:
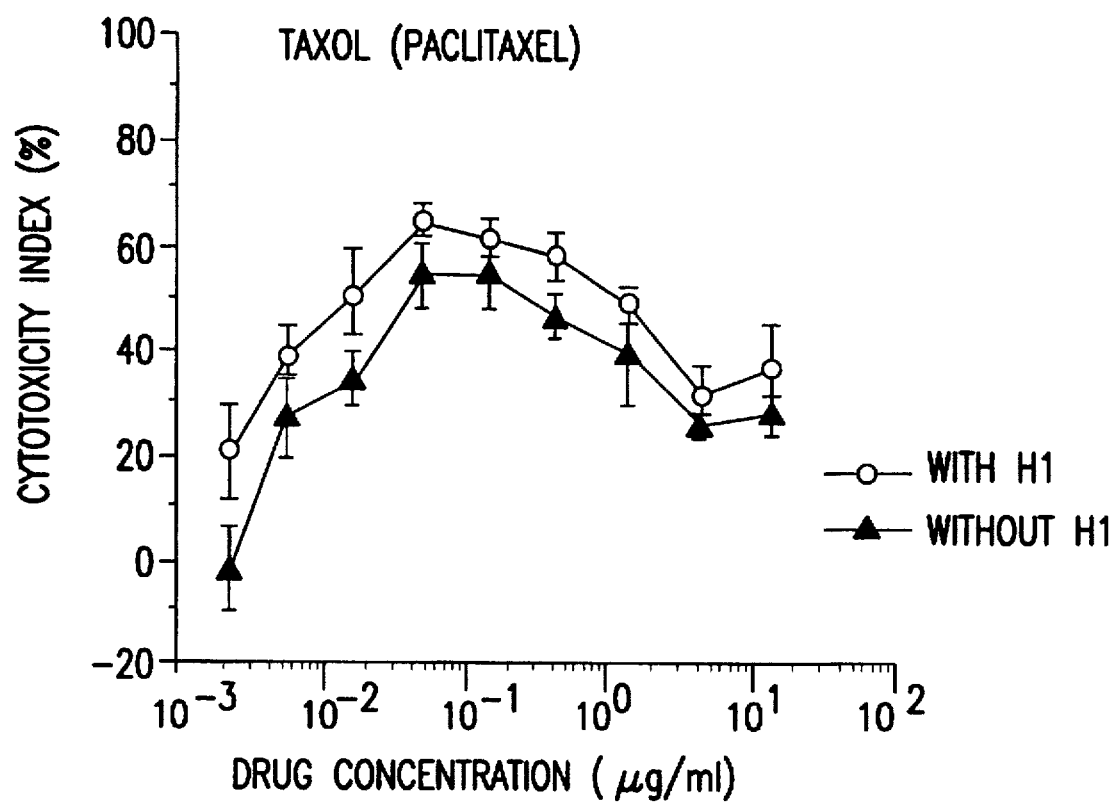

FIGS. 13A, 13B, and 13C shows cytotoxicity indexes of different concentrations of Etoposide (A), Cytosine Arabinofuranoside (B), and Taxol (C) with and without histone H1 150 µg/ml used in co-culture with cells of the Burkitt's lymphoma cell line DAUDI.

Figure 14A:
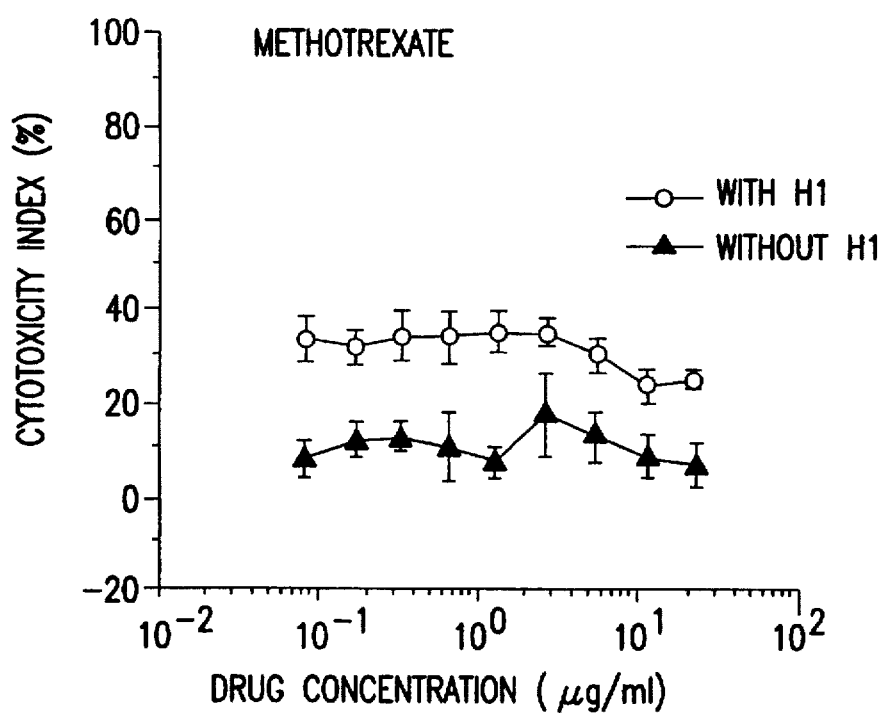
FIGS. 14A, 14B, and 14C are graphs showing cytotoxicity indexes with respect to various drugs.
Figure 14B:
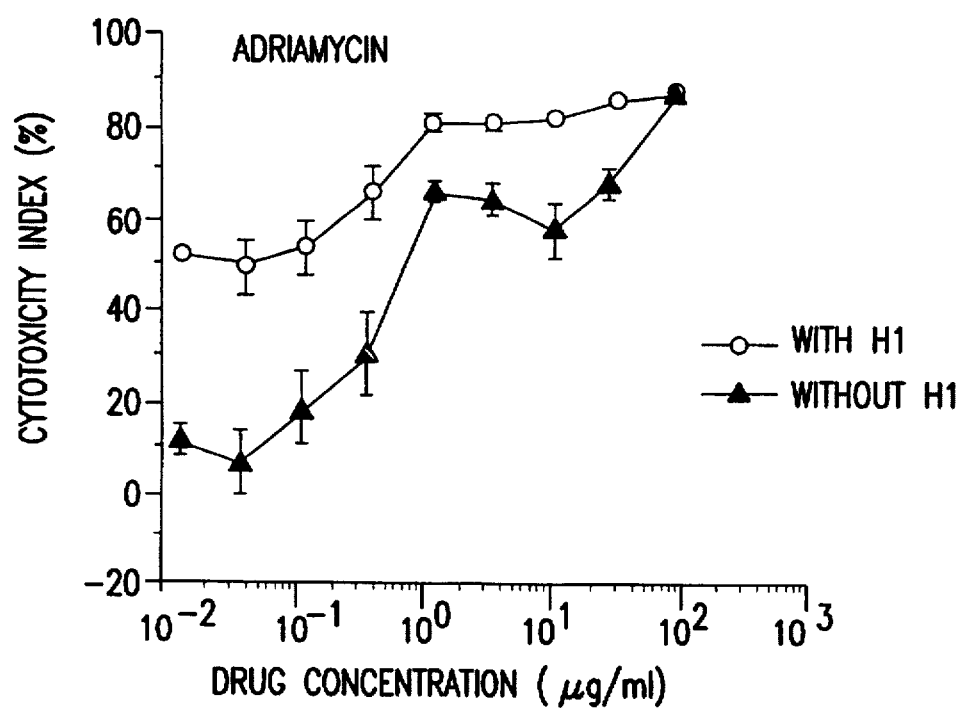
Figure 14C:
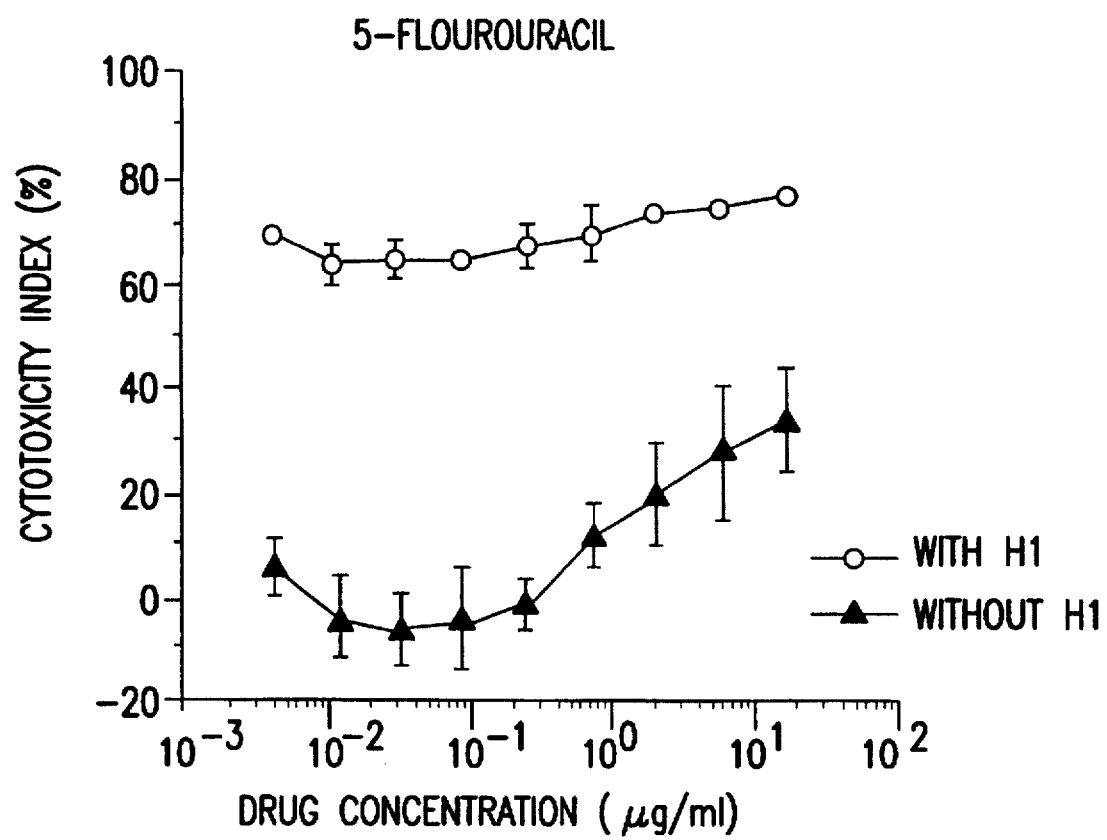

FIGS. 14A, 14B, and 14C show cytotoxicity indexes of different concentrations of Methotrexate (A), Adriamycin (B), and 5-Fluorouracil (C) with and without histone H1 150 µg/ml used in co-culture with cells of the erythroleukemia cell line K562.

Figure 15A:
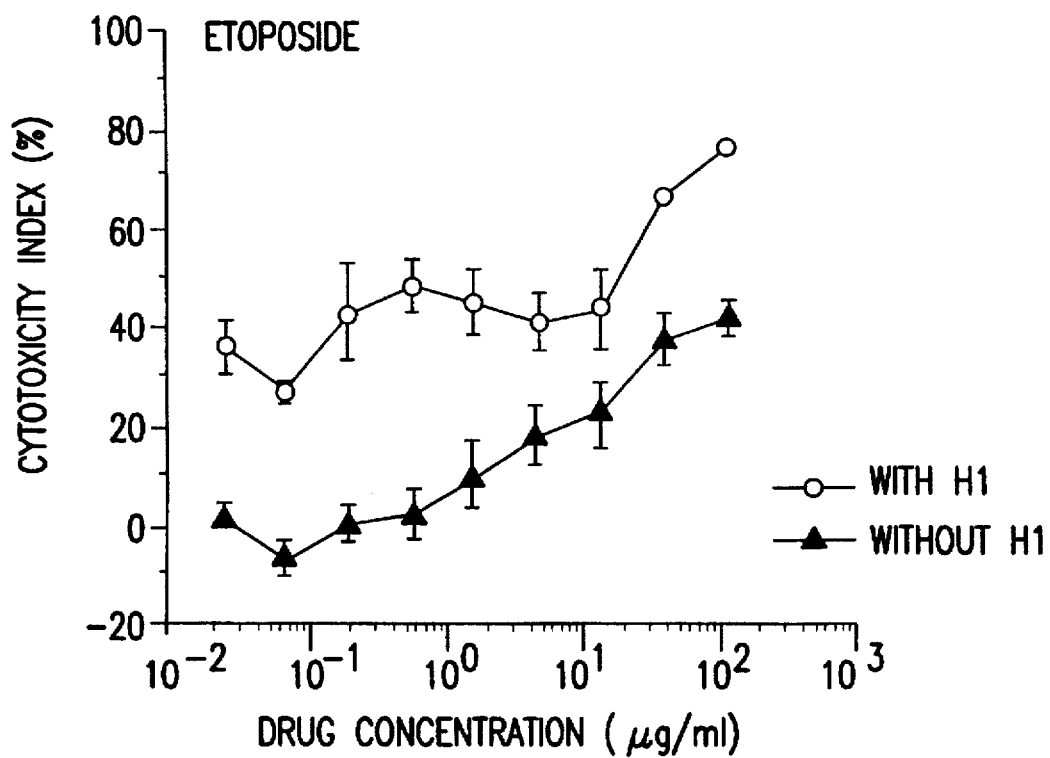
FIGS. 15A, 15B, and 15C are graphs showing cytotoxicity indexes with respect to various drugs.
Figure 15B:
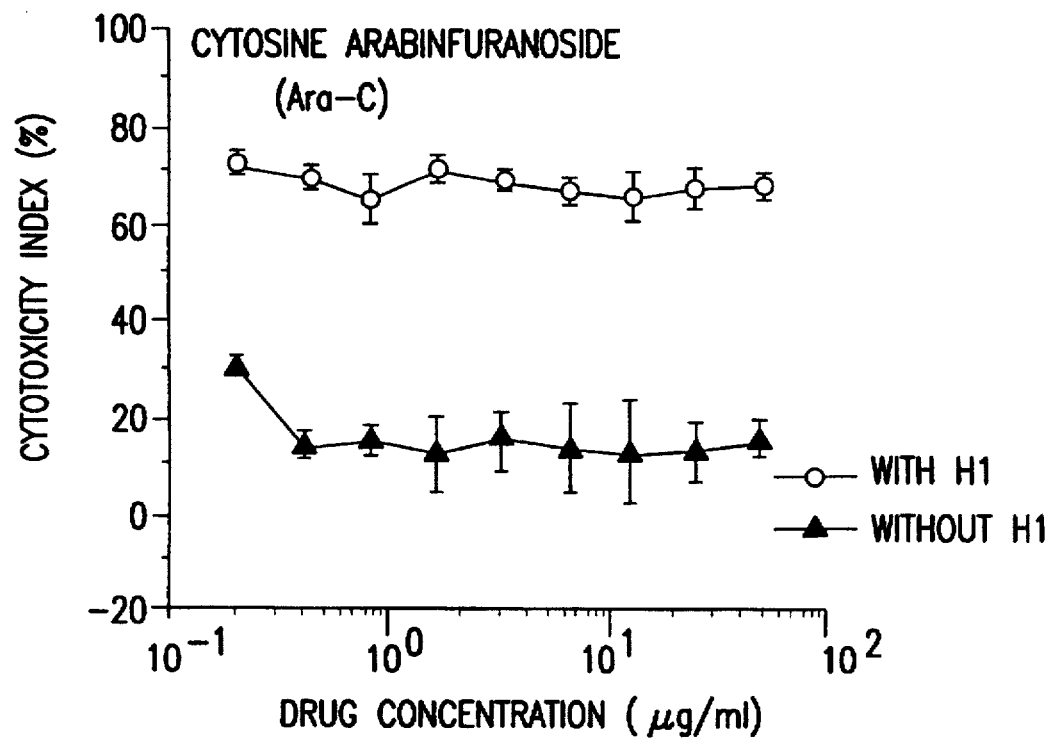
Figure 15C:
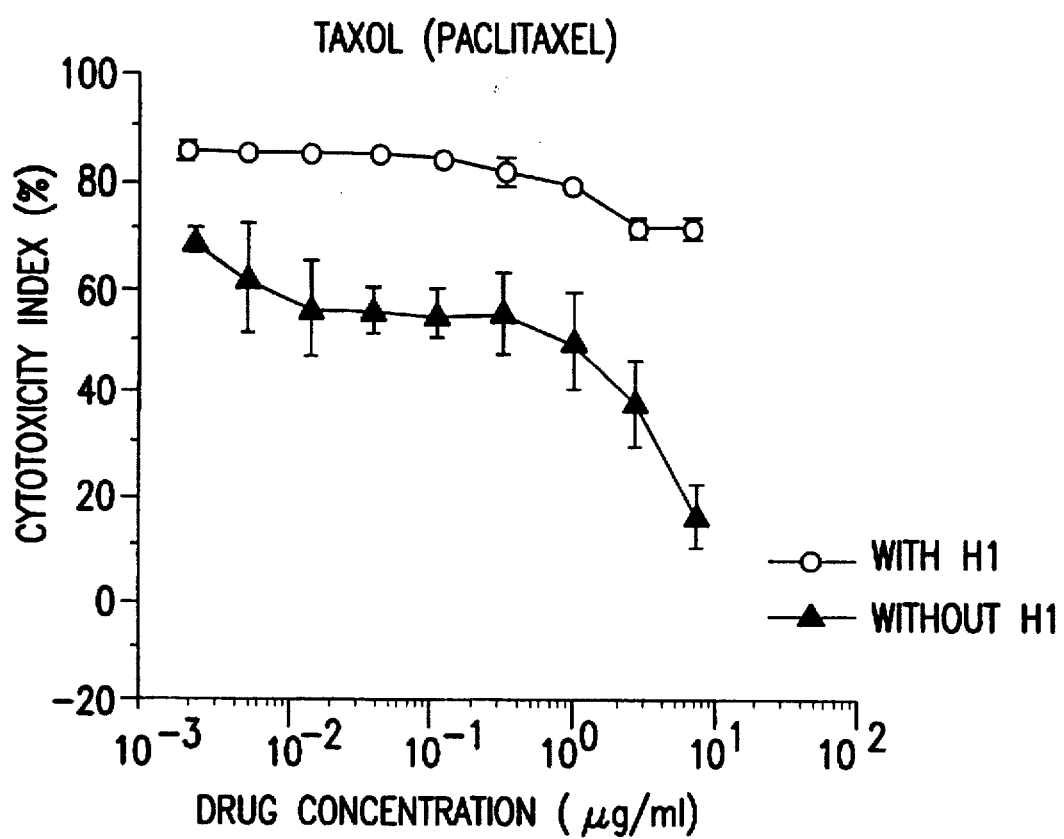

FIGS. 15A, 15B, and 15C show cytotoxicity indexes of different concentrations of Etoposide (A), Cytosine Arabinofuranoside (B), and Taxol (C) with and without histone H1 150 µg/ml used in co-culture with cells of the erythroleukemia cell line K562.

FIG. 16 shows summary of cytotoxicity experiments. The LD50 values are determined graphically and derived from the line graphs (FIGS. 8-15) as the point of intersection of the line connection subsequent concentrations with the LD50 line at the lowest possible drug or drug+histone H1 concentration.

As has been described above, this invention is not restricted to the combination of H2A:H2B, whether it is a mixture or a complex, with cytostatic compounds. It is to be expected that similar effects are observed upon combining the single histones H2A or H2B with cytostatic drugs. It is also expected that comparable effects will be achieved by combining histones H1 and H3 with cytostatic drugs. Furthermore, it is obvious for the expert that entire histone molecules may be replaced by their active parts which are composed of at least four or five amino acid residues exhibiting cytostatic or cytotoxic properties.

Finally, this invention is not limited with respect to the above-mentioned cytostatic compounds. According, the expert has the choice to combine any other suitable cytostatic compound with at least one histone or histone fragment in order to create novel chemotherapeutic drugs possessing increased therapeutic efficiency and enabling lower dosage. The advantages of these combined drugs are:

(i) an increased cytostatic efficiency gained simultaneously with reduced side effects, (ii) the possibility of creating novel, combined chemotherapeutic drugs which exert a cytotoxic action on tumor cells in contrast to a cytostatic effect of the single components of the drug, (iii) the possibility of achieving a positive therapeutic response with cytostatic drugs which alone are inefficient against certain tumor cell lines or certain autoimmune diseases.

Administration of histones (to experimental animals such as mice, rats, guinea pigs, and sheep) does not cause any detectable side effects. Therefore, in accordance with this invention is now possible to perform chemotherapy with a higher chance of success over a longer time period. Simultaneously the extent of side effects may be decreased to an acceptable level.

As to the mode of administration, it should be emphasized that it is the combination of therapeutic agents which gives rise to its synergistic therapeutic effect at the site of the pathogenic process no matter whether the first and the second agent are administered together or separately. Therefore, the two agents may be given together in a single dose or in separate ones with respect to space and time.

Depending on the choice of the first and the second agent and their respective, pharmacokinetic behavior the two substances may be administrated also at different times if this achieves that they reach their optimal concentration at the site of the pathogenic process at a certain time.

Although the experiments described above demonstrate the efficiency of the combination of therapeutic agents according to the invention only with respect to malignant lymphoma and melanoma, the invention is not restricted to the therapy of malignancies. It is obvious to use combinations of therapeutic agents according to this invention also for the treatment of autoimmune diseases.

What is claimed is:

1. A therapeutic method for treatment of carcinoma or autoimmune diseases of a patient, which comprises administering to said patient a biologically active composition which comprises a therapeutically acceptable carrier and, in a quantity having a therapeutic effect, two active substances comprising a pure cytostatic drug as the first active substance and a biologically active pure histone selected from the group consisting of H1, H2A, H2B, H2A:H2B, and H3 as the second active substance, providing a synergistic action of both of said active substances at a site of pathogenic process of said patient.

2. A therapeutic method according to claim 1, wherein said first active substance is selected from the group consisting of vincristine, methotrexate, and cisplatin.

3. A therapeutic method according to claim 2, wherein said second active substance is the dimer H2A:H2B.

4. A therapeutic method according to claim 3, wherein said biologically active composition has anti-melanoma and anti-lymphoma activity.

* * * * *